(12) United States Patent
Ljungmann et al.

(10) Patent No.: US 8,691,583 B2
(45) Date of Patent: Apr. 8, 2014

(54) METHOD AND SYSTEM FOR USE OF TREATMENT LIQUIDS IN AN APPARATUS FOR STAINING OF TISSUE SPECIMENS ON MICROSCOPE SLIDES

(75) Inventors: Øystein Ljungmann, Siggerud (NO); Torstein Ljungmann, Nesoddtangen (NO)

(73) Assignee: Dako Instrumec AS (NO)

( * ) Notice: Subject to any disclaimer, the term of this patent is extended or adjusted under 35 U.S.C. 154(b) by 0 days.

(21) Appl. No.: 13/493,477

(22) Filed: Jun. 11, 2012

(65) Prior Publication Data

US 2012/0309044 A1 Dec. 6, 2012

Related U.S. Application Data

(63) Continuation of application No. 11/793,558, filed as application No. PCT/NO2005/000475 on Dec. 22, 2005, now Pat. No. 8,216,846.

(30) Foreign Application Priority Data

Dec. 23, 2004 (NO) .................................. 20045624

(51) Int. Cl.
*G01N 35/00* (2006.01)
(52) U.S. Cl.
USPC ................... 436/43; 422/63; 422/64; 422/65; 422/536; 436/180

(58) Field of Classification Search
USPC ............ 422/63–67, 50, 500, 43, 536; 436/43, 436/180
See application file for complete search history.

(56) References Cited

U.S. PATENT DOCUMENTS 4,483,270 A * 11/1984 Toya et al. ..................... 118/694
8,216,846 B2 * 7/2012 Ljungmann et al. ............ 436/43

* cited by examiner

*Primary Examiner* — Jyoti Nagpaul
(74) *Attorney, Agent, or Firm* — Finnegan, Henderson, Farabow, Garrett & Dunner, LLP

(57) ABSTRACT

A method and a system for use of treatment liquids in an apparatus for staining of tissue specimens on microscope slides, wherein the apparatus comprises a plurality of vessels (4) for receiving different liquids for treatment of the tissue specimens, a plurality of tanks (11) for treatment liquids, connecting lines (15) between the tanks and the vessels, a plurality of pumps (13) connected on the connecting lines, and a control unit for control of the apparatus and the liquid treatment by means of a data program, wherein the control unit is arranged for selective control of the relevant pumps (13), so that vessels (4) to be used in a staining process, are filled with liquid (14) at the start of the staining process, and so that the liquid-filled vessels (4) are emptied automatically when they are no longer to be used in the staining process.

9 Claims, 4 Drawing Sheets

METHOD AND SYSTEM FOR USE OF TREATMENT LIQUIDS IN AN APPARATUS FOR STAINING OF TISSUE SPECIMENS ON MICROSCOPE SLIDES

This application is a continuation of U.S. application Ser. No. 11/793,558, filed on Jan. 23, 2008 now U.S. Pat. No. 8,216,846, which is a National Stage Entry of International Patent Application No. PCT/NO2005/000475, filed Dec. 22, 2005, and which claims priority benefits from Norwegian Patent Application No. 20045624, filed Dec. 23, 2004, which are incorporated herein by reference.

The invention relates to a method for use of treatment liquids in an apparatus for staining of tissue specimens on microscope slides, wherein the apparatus comprises a plurality of vessels for receiving different liquids for treatment of the tissue specimens, and wherein the liquids are supplied to the vessels from appurtenant tanks via connecting lines with appurtenant pumps, the liquid treatment in the different vessels being controlled by a control unit by means of a data program.

Further, the invention relates to a system for use of treatment liquids in an apparatus for staining of specimens on microscope slides, wherein the apparatus comprises a plurality of vessels for receiving different liquids for treatment of the tissue specimens, a plurality of tanks for treatment liquids, connecting lines between the tanks and the vessels, a plurality of pumps connected on the connecting lines, and a control unit for control of the apparatus and the liquid treatment by means of a data program.

There are previously known a number of different apparatuses for staining of tissue specimens on microscope slides. An apparatus of the type to which the present invention relates, is known from GB 2 196 428 A. Thus, this publication shows an apparatus comprising a plurality of vessels for receiving different reagent liquids for staining of tissue specimens on microscope slides, a plurality of tanks for treatment liquids, line connections between the tanks and the vessels, a plurality of pumps connected on the line connections, and an electronic control unit for controlling the apparatus in accordance with a staining program.

The object of the present invention is to provide a method and a system of the stated type implying a particularly efficient use of the relevant treatment liquids.

An additional object is to provide a method and a system resulting in a substantial increase of the time between maintenance of the treatment liquids.

Additional objects to the invention are to provide a method and a system securing that the quality of the utilized liquids is good, resulting in a drastic reduction of the risk that operator personnel is subjected to dangerous fumes from the liquids, and avoiding degradation of the liquids in that they are subjected unnecessarily to surrounding air.

For achieving the above-mention objects there is provided a method of the introductorily stated type which, according to the invention, is characterised in that the liquids at the start of a staining process are supplied selectively to the relevant vessels to be used in the staining process, and that the liquid-filled vessels are emptied automatically when they are no longer to be used in the staining process.

Further, there is provided a system which is characterised in that the control unit is arranged for selective control of the relevant pumps, so that vessels to be used in a staining process, are filled with liquid at the start of the staining process, and so that the liquid-filled vessels are emptied automatically when they are no longer to be used in the staining process.

An advantageous embodiment of the method is characterised in that the liquids are supplied to the relevant vessel via at least one inlet opening in the bottom of the vessel at an end of the vessel, and are drained via at least one outlet opening in the bottom of the vessel at an opposite side of an overflow wall in relation to the inlet opening, so that there is provided a through-flow of liquid through the vessel by continuous supply of liquid to the vessel by means of the relevant pump. By means of this embodiment it is achieved that there is no need for mechanical agitation for achieving a relative movement between the tissue specimens on the microscope slides and the liquid in the vessels, like in apparatuses according to the prior art, since the through-flow of liquid brings about the necessary movement.

According to an additional advantageous embodiment the liquids are supplied to the vessels via filter means on the respective line connections, to secure thereby that the quality of the liquids is good.

The invention will be further described below in connection with an exemplary embodiment with reference to the drawings, wherein FIG. 1 shows a principle drawing of a multi-function apparatus for, inter alia, staining of tissue specimens on microscope slides, and for placing of cover glasses on microscope slides, wherein the method according to the invention is applied;

Figure 1:
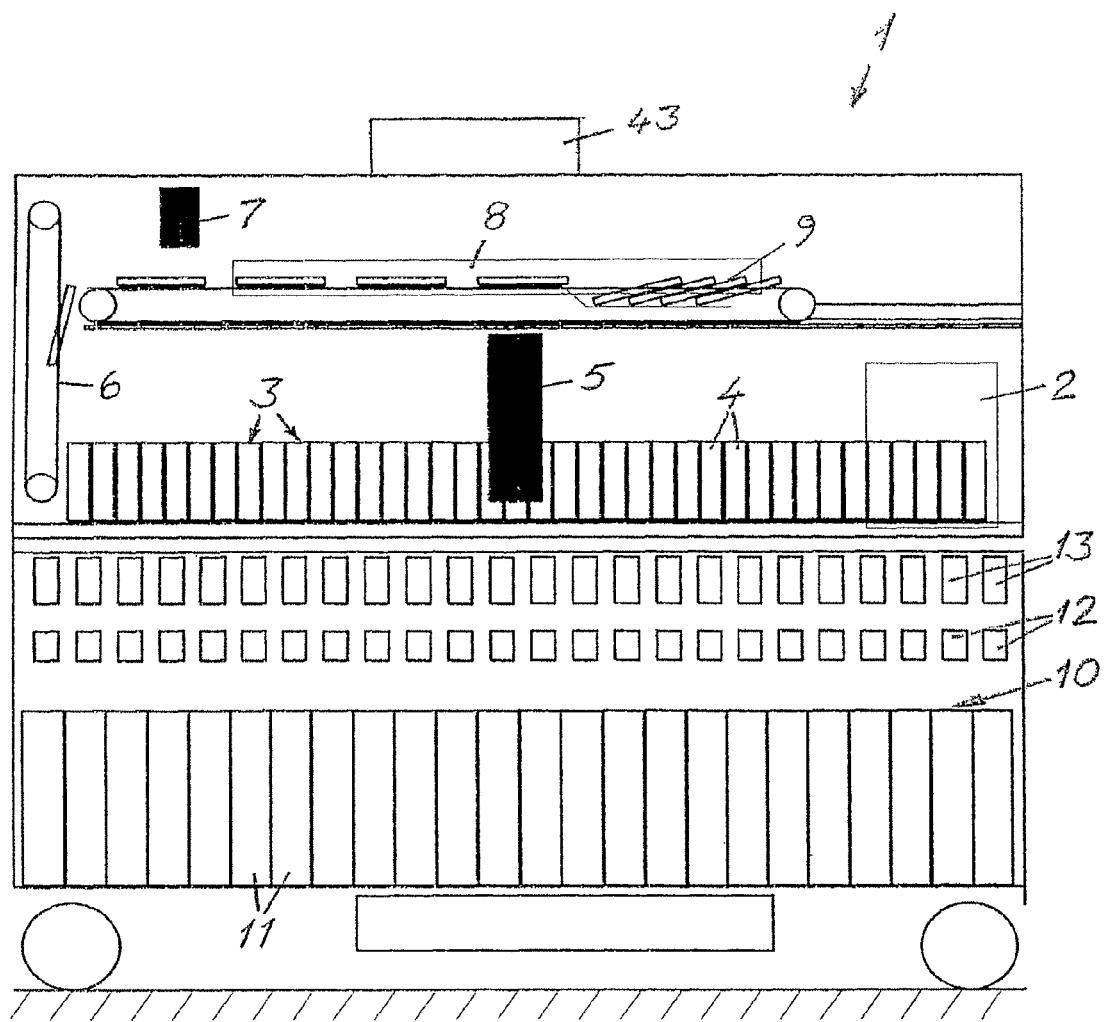

An apparatus 1 for automatic execution of different treatment operations in connection with staining of tissue specimens on microscope slides is shown in FIG. 1. For a further description of the apparatus reference is made to the simultaneously filed international patent application with the title "An apparatus for execution of treatment operations on microscope slides with tissue specimens".

The apparatus 1 is shown to comprise a loading and preheating station 2 for microscope slides (not shown), a plurality of reagent stations 3 consisting of vessels 4 (see FIGS. 5 and 6) for staining of tissue specimens on microscope slides, a conveyor 5 for transfer of carriers (not shown) with microscope slides from vessel to vessel in accordance with a treatment program, a means 6 for transfer of carriers with treated microscope slides from the reagent stations to a station 7 for placing of cover glasses on the stained microscope slides, a succeeding drying station 8 and an unloading station 9 for the ready-treated microscope slides.

The mentioned carriers used in the apparatus, are especially constructed holding devices designed in accordance with the simultaneously filed international patent application with the title "A holding device for microscope slides with tissue specimens". For a further description of this holding device reference is made to said patent application.

As shown in FIG. 1, an array 10 of storage tanks 11 for reagent liquids is arranged under the loading station 2 and the reagent stations 3. The tanks 11 are connected to the reagent vessels 4 via line connections (shown in FIGS. 2-4) on which there are connected respective filters 12 and pumps 13, for transferring the relevant reagent liquids between the tanks the and the vessels in accordance with the method according to the invention, viz. such that the liquids at the start of the staining process are supplied selectively to the relevant vessels to be used in the staining process, and the liquid-filled vessels are emptied automatically when they are no longer to be used in the staining process.

Figure 2B:
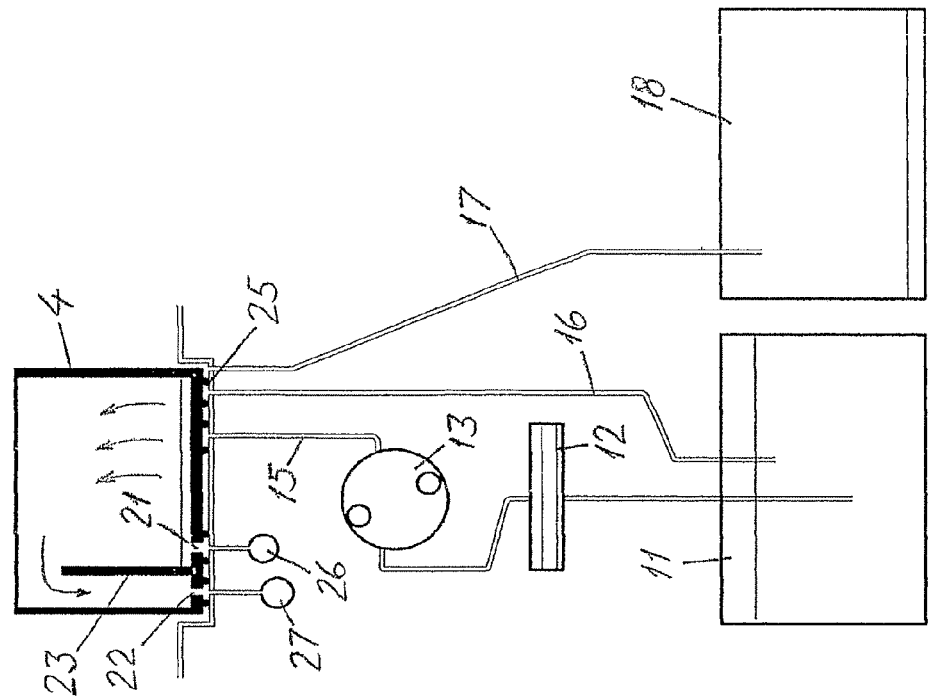
FIGS. 2A-2B show schematically an embodiment of the arrangement for liquid supply from the tanks to the vessels (FIG. 2A), and for possible washing of the vessels with water (FIG. 2B)
Figure 2A:
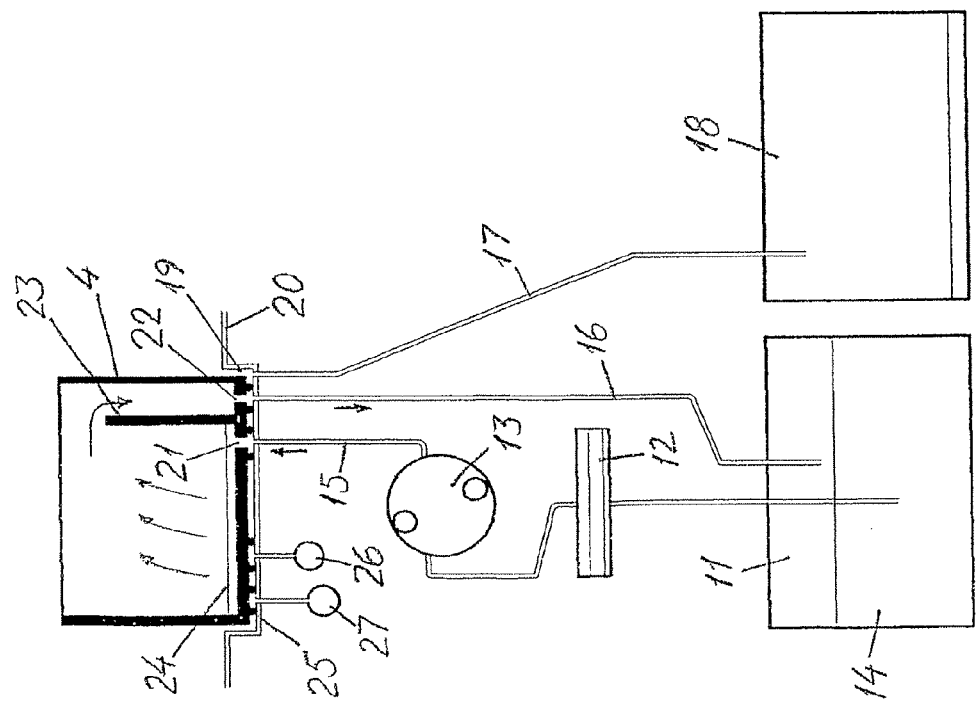

FIG. 2A shows an embodiment of the arrangement for the supply of reagent liquid 14 from a tank 11 to a vessel 4. As appears, a pump 13 and a filter 12 are connected on a supply line 15. The pump preferably is of the peristaltic type, and it is preferably reversible, so that used reagent liquid can be returned to the vessel via the supply line 15. Further, a separate return line 16 is arranged between the vessel 4 and the tank 11, and an exhaust or outlet line 17 is arranged between the vessel and a waste tank 18.

The filters 12, which are provided to secure the quality of the supplied liquids, are shown to be arranged at the suction side of the pumps 13. However, they can with advantage be located at the pumping side of the pumps, for achieving the best possible pump efficiency.

As further appears from FIG. 2A, each of the reagent vessels 4 in the apparatus of FIG. 1 is placed in an appurtenant recess 19 in a carrier plate 20 arranged in the apparatus. In FIGS. 2A and 2B the vessel 4 is shown in a longitudinal section. The vessel is provided with an inlet opening 21 in the bottom of the vessel at one end of the vessel, and with an outlet opening 22 in the bottom of the vessel at an opposite side of an overflow wall 23 in relation to the inlet opening 21, the arrangement being such that a through-flow of liquid is created through the vessel by continuous supply of liquid to the vessel by means of the relevant pump. The through-flow is achieved in that a perforated spreading plate 24 is placed above the bottom of the vessel, so that liquid flowing into the vessel is distributed over the bottom of the vessel under the spreading plate 24, before the liquid flows through the holes in the spreading plate and thereby causes a through-flow of liquid through the whole vessel before it flows over the overflow wall 23 and out of the vessel.

The vessels 4 are releasably mounted in the recesses 19 in the carrier plate 20, and the inlet and outlet openings 21 respectively 22 of the vessels are connected in a sealing manner to the connecting lines 15 and 16 by means of O-ring seals 25 squeezed between the underside of the vessels 4 and the bottom of the recesses 19, when the vessels are put in place in the recesses.

As appears from FIGS. 2A and 2B, a water inlet 26 and a water outlet 27 are arranged in the bottom of the recess 19 at the opposite side of the recess in relation to the inlet for the connecting line 15 and the outlet for the return line 16. The water inlet 26 and the inlet from the connecting line 15 are arranged symmetrically about a midpoint of the vessel, and the same is the case with the water outlet 27 in relation to the outlet to the return line 16. By mounting the vessels 4 in the apparatus in a reversed position, i.e. rotated 180° in relation to the normal operating position in FIG. 2A, it is thereby achieved that the vessels are connected automatically to a system for flushing and cleaning of the vessels with water. This position of the vessel 4 is shown in FIG. 2B. Thus, by means of this arrangement the vessels can be flushed and cleaned without being removed from the apparatus.

In case the O-ring seals 25 in the recesses 19 should not be quite tight, possible leaked-out liquid will be guided from the recess to the waste tank 18 by means of the outlet line 17.

In the embodiment shown in FIG. 2A, the vessel 4 is supplied with reagent liquid from a single appurtenant tank 11. However, a vessel 4 can be supplied with liquid from several tanks in that the connecting lines from these tanks are connected to a multi-way valve connecting the tank to the relevant liquid. Two examples of such alternative embodiments are shown in FIGS. 3 and 4.

Figure 3:
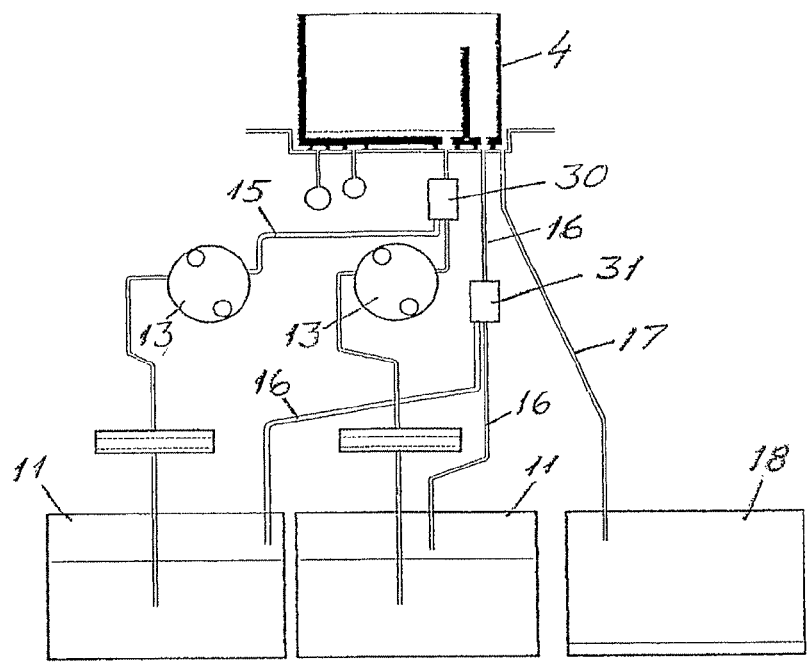
FIG. 3 shows an embodiment wherein liquids from the tanks can be supplied selectively to one and the same vessel by means of a three-way valve connected after two separate pumps.

In the embodiment in FIG. 3 the connecting lines 15 from two tanks 11 are provided with a separate pump 13 which is coupled to a three-way valve 30 having an outlet which is coupled to a vessel 4, so that liquid can be supplied to the vessel from either of the tanks 11. The return line 16 from the vessel 4 is also coupled to a three-way valve 31 having two outlets which are coupled to the return lines 16 to each of the tanks 11, so that the liquid from the vessel can be returned to either of the tanks.

Figure 4:
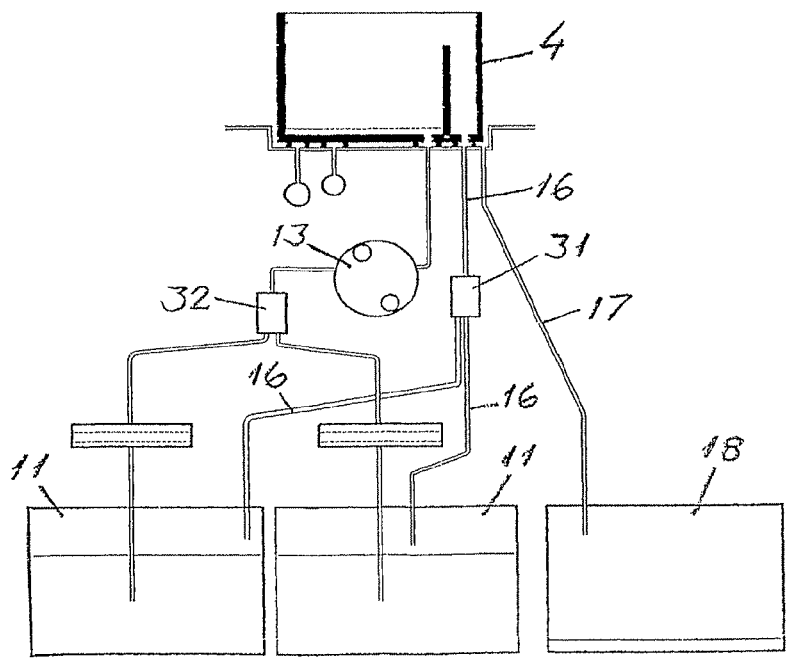
FIG. 4 shows an embodiment wherein liquids from two tanks can be supplied selectively to one vessel by means of a three-way valve connected before a single pump.

In the embodiment in FIG. 4 the connecting lines 15 from two tanks 11 are coupled to a three-way valve 32 having an outlet which is connected to the relevant vessel 4 via a single pump 13, so that liquid from an optional one of the tanks 11 can be supplied to the vessel by means of said pump 13. Also in this case the return line 16 from the vessel 4 is coupled to a three-way valve 31 having two outlets which are coupled to the return lines 16 to each of the tanks 11, so that the liquid from the vessel can be returned to one or the other of the tanks.

Figure 5:
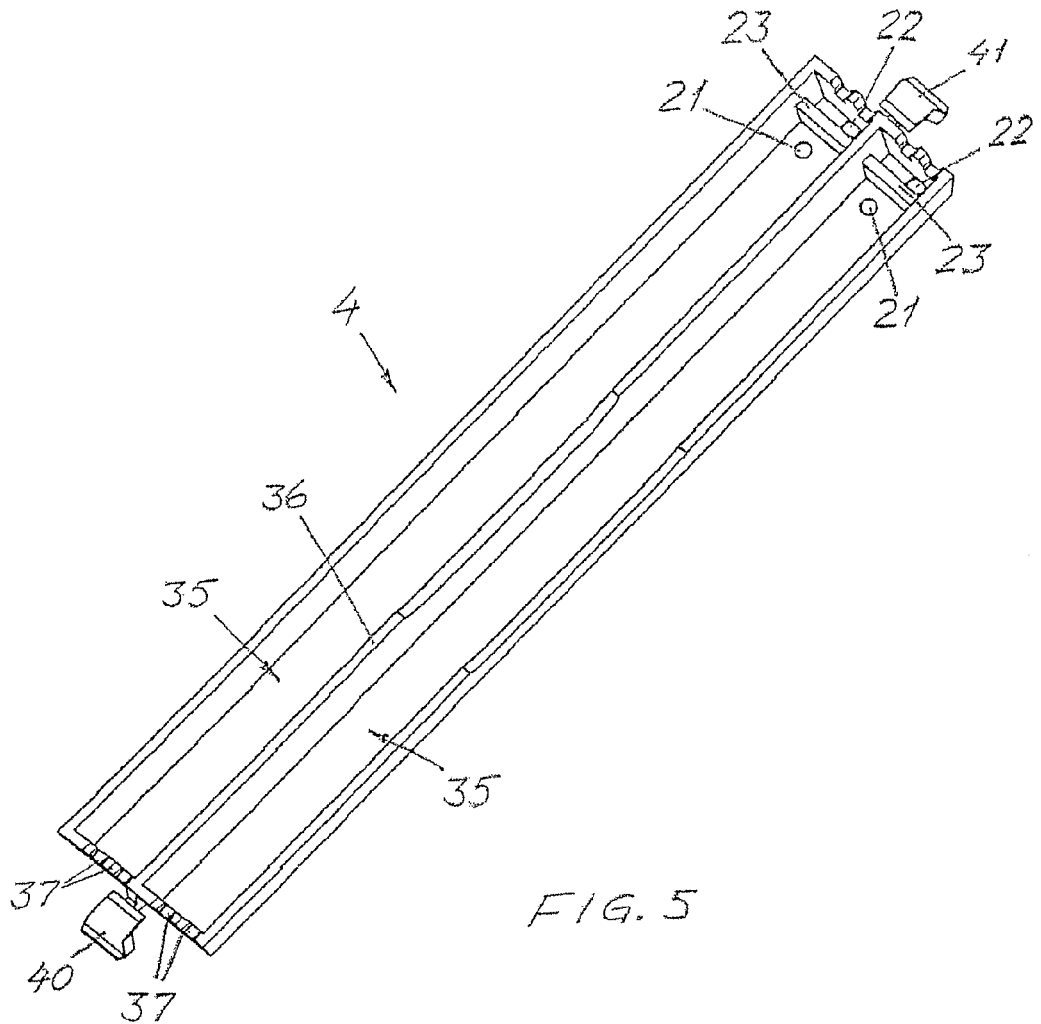
FIG. 5 shows a perspective view seen from above of a vessel arranged for releasable mounting at a staining station in the apparatus of FIG. 1.

A vessel 4 which is arranged for releasable mounting at a staining station in the apparatus of FIG. 1, is shown in FIG. 5. The vessel has an elongated shape and is divided into two parallel spaces 35 by means of a longitudinally extending partition 36. As mentioned above in connection with FIG. 2A, each space 35 is provided with an inlet opening 21 in the bottom of the vessel at one end of the vessel, and with an outlet opening 22 in the bottom of the vessel at an opposite side of an overflow wall 23 in relation to the inlet opening 21.

Each of the end walls of the vessel 4 is provided with four notches 37 for the receipt of suspension portions at the end of carriers or holding devices for microscope slides. As mentioned above, these holding devices are further described in the simultaneously filed patent application having the title "A holding device for microscope slides with tissue specimens".

Figure 6:
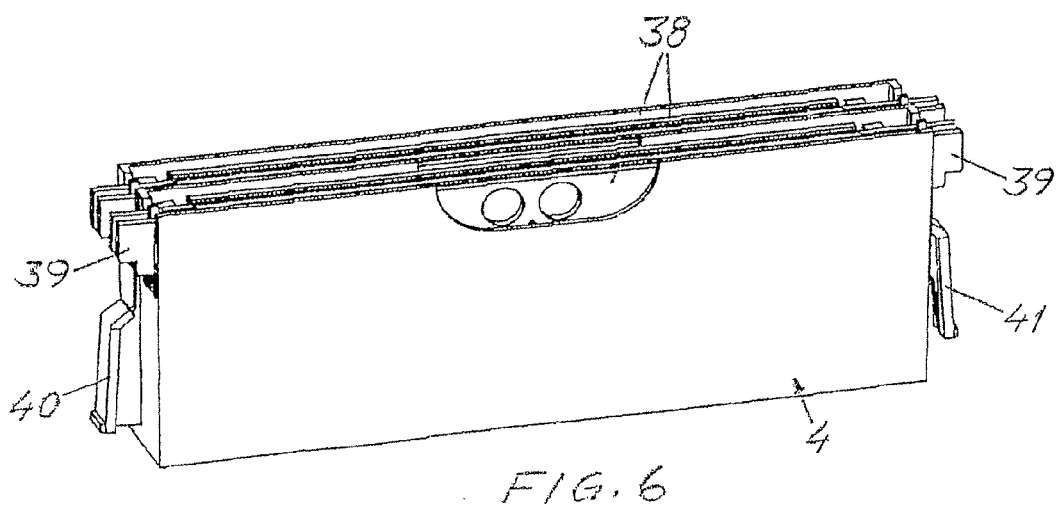
FIG. 6 shows a perspective view of the vessel in FIG. 5 wherein four holding devices with microscope slides are placed in the vessel.

FIG. 6 shows a prospective view of a vessel 4 in which there are placed four holding devices 38, the suspension portions 39 of the holding devices being placed in respective ones of said notches 37. As further appears, the vessel at its ends is provided with fastening members 40 and 41 for releasable mounting of the vessel at the relevant reagent station in the apparatus 1. The fastening member 40 here is a fixed member, whereas the fastening member 1 is resilient, to allow a resilient fixing thereof.

As mentioned above, the apparatus 1 in FIG. 1 is provided with a control unit for controlling the treatment operations of the apparatus in accordance with a data program. In FIG. 1 this control unit is only shown symbolically as a block 43. The control unit preferably comprises a program function by means of which a quality of the liquid in the tanks is measured by means of flown-through liquid quantity in connection with the working life of the liquid.

The apparatus also comprises a non-illustrated control panel for operation of the apparatus. This panel comprises a number of control keys, and also a display giving information about the status of the apparatus during operation.

The invention claimed is:

1. A method for using liquids in an apparatus for staining of tissue specimens on microscope slides, wherein the apparatus comprises at least one vessel wherein the at least one vessel is connected to a supply line comprising a first filter, wherein the supply line connects the at least one vessel to at least one tank carrying liquid for staining the tissue specimen via the first filter;

creating a circulatory system by automatically pumping the liquid for staining the tissue specimen from the at least one tank to the at least one vessel at the start of the staining process and automatically removing the liquid for staining the tissue specimen from the at least one vessel to at least one waste tank through a return line;

wherein the liquid is removed at a time defined by a data program.

2. The method of claim 1, further comprising creating a through-flow system through the at least one vessel by pumping liquid continuously into the vessel and draining liquid continuously from the vessel.

3. The method of claim 1, wherein the at least one tank and the at least one waste tank are the same tanks.

4. The method of claim 1, wherein the at least one vessel comprises the microscope slide.

5. The method of claim 1, wherein the at least one vessel is a reagent station.

6. The method of claim 1, wherein the liquid for staining the tissue specimen is removed from the at least one vessel by draining.

7. The method of claim 1, wherein the liquid for staining the tissue specimen passes through a second filter before reaching the at least one waste tank.

8. The method of claim 1, where the at least one tank has a dedicated pump.

9. The method of claim 1, wherein the liquids are supplied to the at least one vessel though at least one inlet opening in the bottom of the vessel, and are removed via at least one second outlet opening in the bottom of the vessel.

* * * * *